(12) United States Patent
Worman et al.

(10) Patent No.: US 6,627,458 B2
(45) Date of Patent: Sep. 30, 2003

(54) NUCLEAR ENVELOPE PROTEIN RECOGNIZED BY ATYPICAL P-ANCA IN PATIENTS WITH INFLAMMATORY BOWEL DISEASE AND AUTOIMMUNE LIVER DISEASES

(75) Inventors: Howard J. Worman, New York, NY (US); Birgit Terjung, Swisttal (DE)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/882,325

(22) Filed: Jun. 15, 2001

(65) Prior Publication Data

US 2003/0003518 A1 Jan. 2, 2003

(51) Int. Cl.$^7$ ............................................. G01N 33/564
(52) U.S. Cl. ......................... 436/507; 436/508; 435/7.1; 435/7.21
(58) Field of Search ................................ 436/507, 508; 435/7.1, 7.21

(56) References Cited

PUBLICATIONS

Terjung et al., Clinical and Experimental Immunology, vol. 120 S1–p 53, May 2000.*
Terjung et al., Gastroenterology vol. 116, No. 4 part 2, p. A831, Apr. 1999.*
Billing, P., Tahir, S., Calfin, B., Gagne, G., Cobb, L., Targan, S., Vidrich, A. (1995). Nuclear localization of the antigen detected by ulcerative colitis associated perinuclear antineutrophil cytoplasmic antibodies.. Am J Pathol, 147:979–987. (Exhibit 1).
Cohavy, O., Eggena, M.P., Parseghian, M., Hamkalo, B., Targan, S.R., Gordon, L.K., Braun, J., Histone H1. (1997). A candidate pANCA antigen in ulcerative colitis (abstr). Gastroenterology 112:A951. (Exhibit 2).
Cohavy, O., Tayebali, A.B., Phu, P.K., Eggena, M.P., Parseghian, M.H., Hamkalo, B.A., Targan, S., Braun, J. (1998). Characterization of the pANCA cor epitope in the histone H1 C terminus (abstr). Gastroenterology 114:A953. (Exhibit 3).
Courvalin, J.C., Lassoued, K., Bartnik, E., Blobel, G., Wozniak, R.W. (1990). The 210–kD nuclear envelope polypeptide recognized by human autoantibodies in primary biliary cirrhosis is the major glycoprotein of the nuclear pore. J Clin Invest 86:279–285. (Exhibit 4).
Courvalin, J.C., Lassoued, K., Worman, H.J., Blobel, G. (1990). Identification and characterization of autoantibodies against the nuclear envelope lamin B receptor from patients with primary billiary cirrhosis. J Exp Med 172:961–967. (Exhibit 5).
Courvalin, J.C., Worman, H. J., (1997). Nuclear envelope protein autoantibodies in primary biliary cirrhosis. Semin Liver Dis 17: 79–90. (Exhibit 6).

Eggena, M., Targan, S.R., Iwanczyk, L., Vidrich, A., Gordon, L.K., Braun, J. (1996). Phage display cloning and characterization of an immunogentic marker (perinuclear anti–neutrophil cytoplasmic antibody) in ulcerative colitis. J Immunol 156:4005–4011. (Exhibit 7).
Fricker, M., Hollinshead, M., White, N., Vaux, D. (1997). Interphase nuclei of many mammalian cell types contain deep, dynamic, tubular membrane–bound invaginations of the nuclear envelope. J Cell Biol 136: 531–544. (Exhibit 8).
Halbwachs–Mecarelli, L., Nusbaum, P., Noel, L.H., Reumaux, D., Erlinger, S., Grunfeld, J.P., Lesavre, P. (1992). Antineutrophil cytoplasmic antibodies (ANCA) directed against cathespin G inulcerative colitis, Crohn's disease and primary sclerosing cholangitis. Clin Exp Immunol 90:79–84. (Exhibit 9).
Lassoued, K., Guilly, M–N., Danon, F., Andre, C., Dhumeaux, D., Clauvel, J.P., Brouet, J.C., Seligmann, M., Courvalin, J.C. (1988). Antinuclear autoantibodies specific for lamins: characterization and clinical significance. Ann Intern Med 108:829–833. (Exhibit 10).
Lassoued, K., Brenard, R., Degos, F., Courvalin, J.C., Andre, C., Danon, F., Brouet, J.C., Zine–el–Abidine, Y., Degott, C., Zafrani, S., Dhumeaux, D., Benhamou, J.P. (1990). Antinuclear antibodies directed to a 200–kilodalton polypeptide of the nuclear envelope in primary biliary cirrhosis. A clinical and immunological study of a series of 150 patients with primary biliary cirrhosis. Gastroenterology 99:181–186. (Exhibit 11).
Mizoguchi, E., Mizoguchi, A., Chiba, C., Niles, J.L., Bhan, A.K. (1997). Antineutrophil cytoplasmic antibodies in T–cell receptor alpha–deficient mice with chronic colitis. Gastroenterology 113:1828–1835. (Exhibit 12).

(List continued on next page.)

*Primary Examiner*—Patrick J. Nolan
(74) *Attorney, Agent, or Firm*—John P. White; Cooper & Dunham LLP

(57) ABSTRACT

The present invention is directed to the molecular characterization of the nuclear antigen recognized by atypical p-antineutrophil cytoplasmic antibodies (p-ANCA) in order to better diagnose patients with inflammatory bowel diseases such as ulcerative colitis (UC), and autoimmune liver diseases such as primary sclerosing cholangitis (PSC) and autoimmune hepatitis (AIH). Molecular characterization of the target antigen comprises preparing cytoplasmic and nuclear extracts of human neutrophils, human HL-60 and murine 32D myeloid cells. Proteins should then be resolved by 1 and 2 dimensional gel electrophoresis and reactive proteins can then be detected by immunoblotting with sera from individuals, making certain to have both normal and disease controls. Atypical p-ANCA should then be affinity purified against the reactive protein and investigated for their immunofluorescence pattern using confocal microscopy. One could then detect the antigen that atypical p-ANCA can recognize and use that antigen to detect the prescence of atypical p-antineutrophil cytoplasmic antibodies so as to diagnose patients with inflammatory bowel diseases such as ulcerative colitis (UC), and autoimmune liver diseases such as sclerosing cholangitis (PSC) and autoimmune hepatitis (AIH).

6 Claims, 7 Drawing Sheets

OTHER PUBLICATIONS

Nickowitz, R.E., Wozniak, R.R. Schaffner, F., Worman, H.J. (1994). Autoantibodies against integral membrane proteins of the nuclear envelope in patients with primary biliary cirrhosis. Gastroenterology 106:193–199. (Exhibit 13).

Peen, E., Almer, S., Bodemar, G., Ryden, B.O., Sjöjlin, C., Tejle, K., Skogh, K. (1993). Anti–lactoferrin antibodies and other types of ANCA in ulcerative colitis, primary sclerosing cholangitis, and Crohn's disease. Gut 34:56–62. (Exhibit 14).

Roozendaal, C., Zhao, M.H., Horst, G., Lockwood, C.M., Kleibeuker, J.H., Limburg, P.C., Nelis, G.F., Kallenberg, C.G.M. (1998). Catalase and a–enolase: two novel granuloycte antigens in inflammatory bowel disease (IBD). Clin Exp Immunol 112:10–16. (Exhibit 15).

Saviage, J., Gillis, D., Benson, E., Davies, D., Esnault, V., Falk, R.J., Hagen, E.C., Jayne, D., Jennette, J.C., Paspaliaris, B., Pollock, W., Pusey, C., Savage C.O.S., Silvestrini, R., van der Woude, F., Wieslander J., Wiik, A. (1999). International consensus statement on testing and reporting of antineutrophil cytoplasmic antibodies (ANCA). Am J Clin Pathol 111:507–513. (Exhibit 16).

Sobajima, J., Ozaki, S., Osakada, F., Uesugi, H., Shirakawa, H., Yoshida, M., Nakao, K. (1997) Novel autoantigens of perinuclear anti–neutrophil cytoplasmic antibodies (p–ANCA) in ulcerative colitis: non–histone chromosomal proteins, HMG1 and HMG2. Clin Exp Immunol 107:135–140. (Exhibit 17).

Sobajima, J., Ozaki, S., Uesugi, H., Osakada, F., Inoue, M., Fukuda, Y., Shirakawa, H., Yoshida, M., Rokuhara, A., Imai, H., Kiyosawa, K., Nakao, K. (1999). High mobility group (HMG) non–histone chromosomal proteins HMG1 and HMG2 are significant target antigens of perinuclear anti–neutrophil cytoplasmic antibodies in autoimmune hepatitis. Gut 44:867–873. (Exhibit 18).

Terjung, B., Herzog, V., Worman, H.J., Gestmann, I., Bauer, C., Sauerbruch, T., Spengler, U. (1998). Atypical antineutrophil cytoplasmic antibodies with perinuclear fluoresence in chronic inflammatory bowel disease and hepatobiliary disorders colocalize with nuclear lamina proteins. Hepatology 28:332–340. (Exhibit 19).

Walmsley, R.S., Zhao, M.H., Hamilton, M.I., Brownlee, A., Chapman, P., Pounder, R.E., Wakefield, A.J., Lockwood, C.M. (1997). Antineutrophil cytoplasm autoantibodies against bactericidal/permeability–increasing protein in inflammatory bowel disease. Gut 40:105–109. (Exhibit 20).

Wesierska–Gadek, J., Penner, E., Hitchmann, E., Sauermann, G. (1988). Antibodies to nuclear lamins in autoimmue liver disease. Clin Immunol Immunopathol 49:107–115. (Exhibit 21).

Worman, H.J., Yuan, J., Blobel, G., Georgatos, S.D., (1988). A Lamin B receptor in the nuclear envelope. Proc Natl Acad Sci USA 85:8531–8534. (Exhibit 22).

Worman, H.J., Evans, C.D., Blobel, G. (1990). The lamin B receptor of the nuclear envelope inner membrane: apolytopic protein with eight potential transmembrane domains. J Cell Biol 111:1535–1542. (Exhibit 23).

Worman, H.J., Couvalin, J.C. (1991). Autoantibodies against nuclear envelope proteins in liver diseases. Hepatology 14:1269–1279. (Exhibit 24).

Woude van der F.J., Lobatoo, S., Permin H., van der Giessen M, Rasmuseen N., Wiik, A., van Es L.A., van der Herm. G.K., (1985). The TH. Autoantibodies against neutrophils and monocytes: tools for diagnosis and marker of disease activity in Wegener's granulomatosis. Lancet 1:425–429. (Exhibit 25).

Terjung, B., Spengler, U., T. and Worman, H.J. "Atypical pANCA" in IBD and hepatobiliary disorders react with a 50 kD nuclear envelope protein of neutrophils and myeloid cells. Gastroenterology 2000;119:310–322 (Exhibit 26).

* cited by examiner

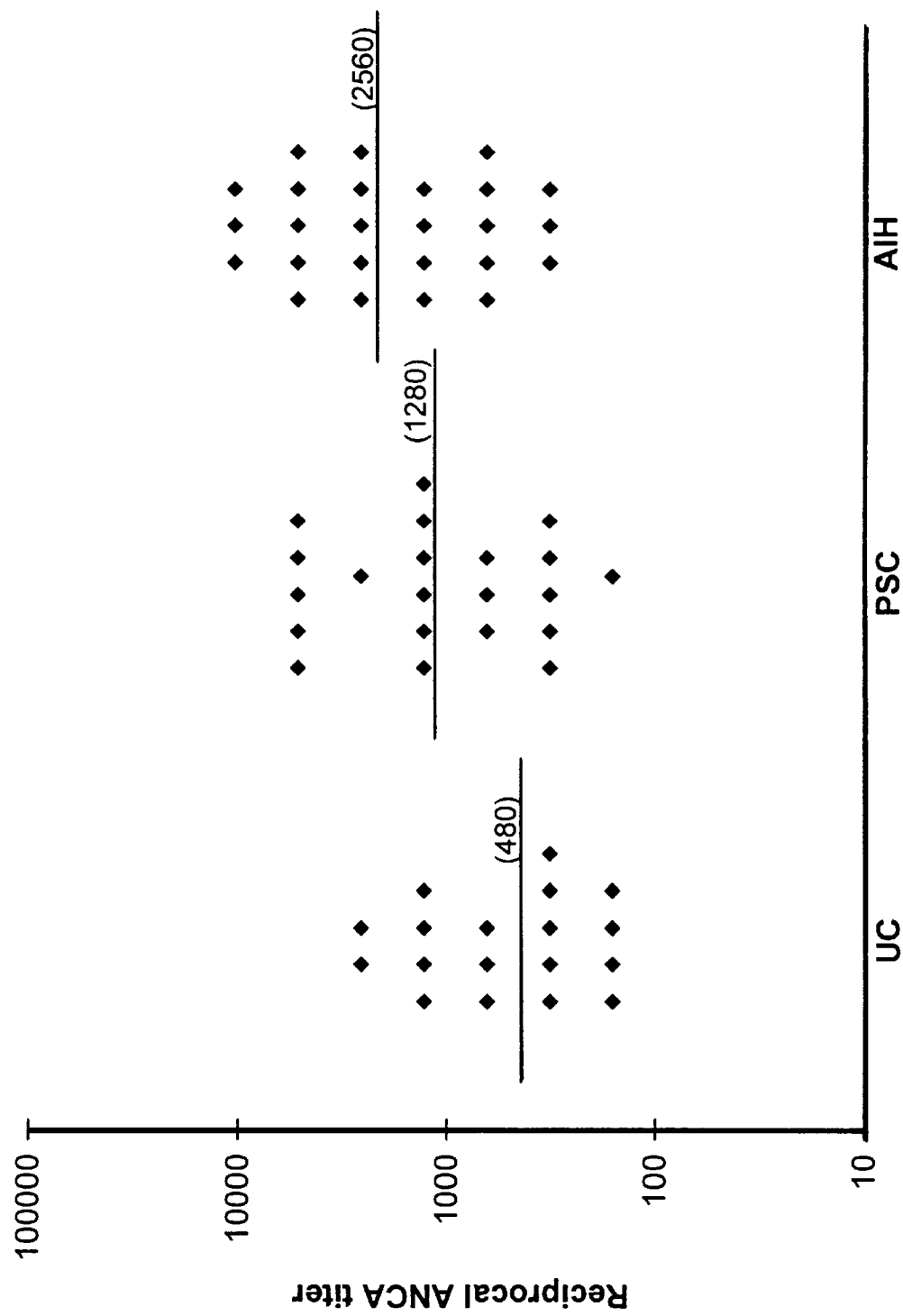

non affinity-purified
atypical p-ANCA + ANA affinity-purified
atypical p-ANCA

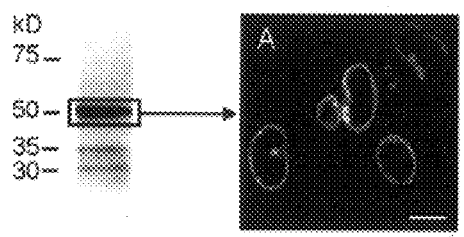 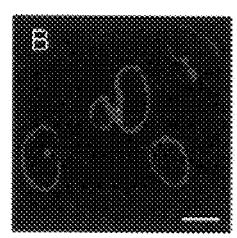 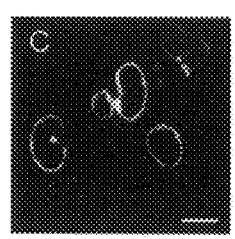
FIGURE 6A   FIGURE 6B   FIGURE 6C
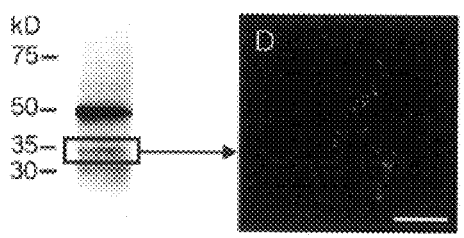 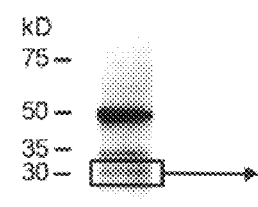
FIGURE 6D   FIGURE 6E

NUCLEAR ENVELOPE PROTEIN RECOGNIZED BY ATYPICAL P-ANCA IN PATIENTS WITH INFLAMMATORY BOWEL DISEASE AND AUTOIMMUNE LIVER DISEASES

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Atypical "antineutrophil cytoplasmic antibodies" (ANCA) are present in patients with ulcerative colitis (UC), primary sclerosing cholangitis (PSC), and autoimmune hepatitis (AIH) ANCA represent a family of heterogenous autoantibodies directed against constituents of neutrophilic granulocytes. These autoantibodies have become valuable seromarkers for the diagnostic and therapeutic management of patients with systemic vasculitides such as Wegner granulomatosis and microscopic polyangiitis, in which they recognize well defined cytoplasmic antigens such as proteinase 3 and myeloperoxidase. Two well established ANCA staining patterns can be distinguished on ethanol-fixed neutrophils: a difuse cytoplasmic fluorescence pattern (c-ANCA) and a fine homogeneous labeling of the perinuclear cytoplasm (p-ANCA).

Autoantibodies that are similar to p-ANCA in patients with systemic vasculitides are detected in individuals with chronic inflammatory bowel diseases (IBD) such as ulcerative colitis or autoimmune liver disorders such as primary sclerosing cholangitis (PSC) and autoimmune hepatitis (AIH). Contrary to systemic vasculitides, the role of ANCA in these disorders is not clear. Various cytoplasmic proteins such as bactericidal/permeability increasing protein, catalase, cathepsin G, enolase, or lactoferrin have been proposed as putative target antigens of ANCA in these disorders, but reactivity to these proteins has only been detected in less than thirty five percent of cases. The predominant target antigen of ANCA in IBD and autoimmune liver disorders has not been identified. Since their target antigens are unknown, p-ANCA in patients with IBD or autoimmune liver disorders are generally referred to as atypical p-ANCA.

ANCA are generally defined as autoantibodies directed against cytoplasmic antigens localized in the azurophil and specific granules of neutrophils (Woude et al., 1985; Savige et al, 1999). Using double-labeling immunofluorescence microscopy, it was shown that this definition holds true only for C-ANCA and classic p-ANCA in systemic vasculitides, but not for ANCA in individuals with IBD and autoimmune liver disease (Billing et al, 1995; Terjung et al., 1998). ANCA in those disorders do not react with cytoplasmic structures (Billing et al, 1995; Terjung et al., 1998). Their fluorescence pattern examined by indirect immunofluorescence microscopy is characterized by a broad inhomogeneous labeling of the nuclear periphery along with multiple intranuclear fluorescent foci. By means of immuno electron microscopy, it has been shown that this focal intranuclear fluorescence likely corresponds to invaginations of the nuclear envelope (Fricker et al., 1997; Terjung et al., 1998). These labeling characteristics of atypical p-ANCA in IBD and autoimmune liver disorders strongly suggest that a nuclear antigen is the target (possibly the term ANCA (antineutrophil cytoplasmic antibody) is a misnomer, and the term ANNA (antineutrophil nuclear antibody) is more appropriate).

Previously, it has been suggested that histone H1, particularly its isoform H1–3, is a candidate antigen recognized by atypical p-ANCA in patients with UC (Targan et al., 1996; Cohavy et al., 1997,; and Cohavy et al. 1998). Furthermore, reactivity to this nuclear antigen in 42 percent of sera from T-cell receptor alpha-deficient mice that developed UC like syndrome and whose sera contained ANCA has also been reported (Mizoguchi et al., 1997). In addition, eighty nine percent of sampled patients with AIH had antibodies that recognized high mobility group (HMG ½) non-histone chromosomal proteins (Sobajima et al., 1997). Although neither histone H1 nor HMG ½ proteins are neutrophil specific, it has been hypothesized that certain epitopes of these nuclear proteins are only immunoaccessible in neutrophils and therefore might represent target proteins of atypical p-ANCA (Targan et al., 1996; Cohavy et al., 1997,; and Cohavy et al. 1998). However, these studies do not exclude the possibility that atypical p-ANCA predominantly recognize another myeloid specific nuclear protein.

Therefore, a need arises to characterize the nuclear antigen recognized by atypical p-ANCA. The main impetus behind this need is that molecular identification of the target antigen will result in the development of highly specific, sensitive, and reproducible assays for the detection of atypical p-ANCA in the routine clinical laboratory setting. These assays will have diagnostic use for patients with IBD, in particular UC and autoimmune liver disorders, in particular PSC ans AIH.

SUMMARY OF THE INVENTION

The present invention is directed to the molecular characterization of the nuclear antigen recognized by atypical p-antineutrophil cytoplasmic antibodies (p-ANCA), thus permitting better diagnosis of patients with inflammatory bowel diseases such as ulcerative colitis (UC), and autoimmune liver diseases such as primary sclerosing cholangitis (PSC), and autoimmune hepatitis (AIH). Molecular characterization of the target antigen comprises preparing cytoplasmic and nuclear extracts of human neutrophils, human HL-60 and murine 32D myeloid cells. Proteins are resolved by 1 and 2 dimensional gel electrophoresis and reactive proteins are detected by immunoblotting with sera from individuals, making certain to have both normal and disease controls. Atypical p-ANCA can further be affinity purified against the reactive protein and investigated for their immunofluorescence pattern using confocal microscopy. The antigen that atypical p-ANCA can recognize is isolated or partially purified and used to detect the presence of atypical p-antineutrophil cytoplasmic antibodies so as to diagnose patients with inflammatory bowel diseases such as ulcerative colitis (UC), and autoimmune liver disease such as primary sclerosing cholangitis (PSC) and autoimmune hepatitis (AIH).

BRIEF DESCRIPTION OF THE FIGURE

FIG. 1: Distribution of the serum titers of atypical p-ANCA with respect to the underlying disease. The endpoint serum titers of atypical p-ANCA were assessed by indirect immunofluorescence microscopy on ethanol-fixed neutrophilis. The solid line indicates the median endpoint serum titers of ANCA with respect to the underlying disease. The median serum titers of atypical p-ANCA in patients with PSC (n=21) and AIH (n=25) were markedly higher than in patients with UC (n=18) (1:1280 and 1:2560 vs. 1:480).

FIG. 6: Immunofluorescence patterns of affinity-purified antibodies on ethanol-fixed HL-60 cells examined by confocal laser scanning microscopy. We performed double labeling of ethanol-fixed HL-60 cells with antibodies affinity-purified against the 50-kilodalton nuclear envelope protein and antibodies against rabbit lamin B1. FITC-conjugated goat anti-human lgG secondary antibodies were used to detect ANCA (green). Texas red-conjugated goat anti-rabbit lgG was used to detect antibodies against lamin B1 (red). Yellow staining indicates colocalization of both fluorescence signals when they were optically superimposed. The serum used for the affinity-purification was from a patient with active PSC. (A) atypical p-ANCA affinity-purified against the 50-kilodalton nuclear envelope protein gave a rim-like peripheral nuclear labeling with intranuclear fluorescent foci on ethanol-fixed differentiated HL-60 cells. This fluorescence pattern was similar to the staining patterns shown for nonpurified sera containing atypical p-ANCA in FIG. 1. (B and C) The fluorescence pattern of the affinity-purified atypical p-ANCA was identical to the fluorescence pattern of antibodies against lamin B1 (B). Yellow staining indicates colocalization (C). (D and E) On immunoblots of nuclear extracts from HL-60 cells incubated with atypical p-ANCA, 2 further reactive nuclear proteins with apparent molecular masses of 35 and 30 kilodaltons, but with a significantly weaker signal intensity than that of the 50-kilodalton protein, were detected. Antibodies affinity-purified against these proteins only gave a weak nonspecific cytoplasmic background fluorescence on ethanol-fixed HL-60 cells. For immunoblots, migration of molecular mass standards is indicated in kilodaltons. Bars=10 μm. Affinity-purified antibodies used for immunofluorescence microscopy were diluted 1:80.

DETAILED DESCRIPTION OF THE INVENTION

Figure 2A:
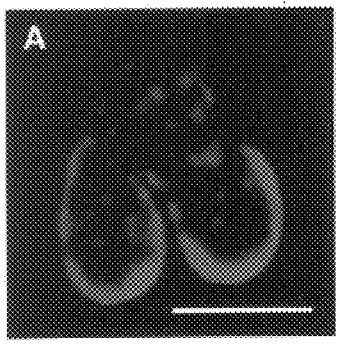
FIG. 2: Fluorescence patterns of atypical p-ANCA on ethanol-fixed human neutrophils, HL-60, and 32D cells examined by confocal laser scanning microscopy. ANCA were detected with FITC-conjugated goat anti-human lgG secondary antibodies. Antibodies to lamin B1 were visualized by Texas red-conjugated goat anti-rabbit lgG secondary antibodies. When the fluorescence signal of ANCA (green) and the fluorescence labeling of antibodies against lamin B1 (red) were optically superimposed, a colocalization of both signals was indicated by yellow staining. (A) A broad inhomogeneous rim-like nuclear fluorescence along with scattered intranuclear fluorescent foci was observed with atypical p-ANCA on ethanol-fixed neutrophils. (B and C) A fluorescence pattern similar to that obtained with human neutrophils was detected on ethanol-fixed differentiated HL-60 cells (B), as well as on ethanol-fixed differentiated 32D cells (C). This stage of cell differentiation to mature banded or segmented myeloid cells was first observed 5 days after induction by dimethylsulfoxide. (D and E) Because the nucleus of undifferentiated HL-60 and 32D cells is not lobulated, the promyelocytic HL-60 cells (D) and the myelocytic 32D cells (E) lack the scattered intranuclear fluorescent foci, probably corresponding to invaginations of the nuclear envelope. (F) A few intranuclear fluorescent foci (arrows) indicate the beginning nuclear segmentation of HL-60 cells differentiated to metamyeclocytes. This stage of cell differentiation was observed 4 days after induction by dimethylsulfoxide. (G to l) The fluorescence pattern obtained with atypical p-ANCA (G) on ethanol-fixed immature HL-60 cells was identical to the fluorescence labeling observed with antibodies against lamin B1 (H). (1) Optically superimposed images. Bars=10 $\mu$m. Sera were diluted 1:20 for use in immunofluorescence microscopy.

The present invention is directed to the molecular characterization of the nuclear antigen recognized by atypical p-antineutrophil cytoplasmic antibodies (p-ANCA), thus permitting better diagnosis of patients with an inflammatory bowel disease such as ulcerative colitis (UC), and an autoimmune liver disease such as primary sclerosing cholangitis (PSC) or autoimmune hepatitis (AIH). Molecular characterization of the target antigen comprises preparing cytoplasmic and nuclear extracts of human neutrophils, human HL-60 and murine 32D myeloid cells. Proteins are resolved by 1 and 2 dimensional gel electrophoresis and reactive proteins are detected by immunoblotting with sera from individuals, making certain to have both normal and disease controls. Atypical p-ANCA can also be affinity purified against the reactive protein and investigated for their immunofluorescence pattern using confocal microscopy. The antigen that atypical p-ANCA can recognize is isolated or partially purified and used to detect the presence of atypical p-antineutrophil cytoplasmic antibodies so as to diagnose patients with an inflammatory bowel disease such as ulcerative colitis (UC), and an autoimmune liver disease such as primary sclerosing cholangitis (PSC) or autoimmune hepatitis (AIH).

A substantially purified nuclear envelope protein of neutrophils and myeloid cells having a molecular weight of 40,000–60,000 Daltons, more specifically a molecular weight of 45,000–55,000 Daltons, yet more specifically an apparent molecular weight of about 50,000 Daltons as estimated by SDS-polyacrylamide gel electrophoresis, and capable of binding with atypical p-antineutrophil cytoplasmic antibodies (p-ANCA).

This present invention has achieved the identification of a nuclear target antigen having an apparent molecular weight of about 50,000 Daltons as estimated by SDS-polyacrylamide gel electrophoresis, with an isoelectric point of approximately pH 6.0 of atypical p-antineutrophil cytoplasmic antibodies (atypical p-ANCA) which is found exclusively in myeloid cells. This target antigen is recognized by 92% of atypical p-ANCA in inflammatory bowel disease or autoimmune liver disease as opposed to atypical p-ANCA's 25%–30% reported reactivity rate with putative cytoplasmic target antigens (Walmsey et al., 1997).

Identification of this specific target antigen has led to an understanding as to how atypical p-ANCA is involved in the immunopathogenesis of inflammatory bowel diseases such as ulcerative colitis (UC), and autoimmune liver diseases such as primary sclerosing cholangitis (PSC) or autoimmune hepatitis (AIH). Moreover, identification of this target antigen results in the development of highly specific, sensitive, and reproducible assays for the detection of atypical p-ANCA in routine clinical laboratory settings.

Therefore, this invention provides a method for detecting the presence of atypical p-ANCA, thus providing a diagnostic use, e.g. for patients with an inflammatory bowel disease or an autoimmune liver disease.

This invention provides for a diagnostic kit comprising of a support where the 50,000 Dalton nuclear envelope protein of neutrophils and myeloid cells, with an isoelectric point of approximately pH 6.0, capable of binding with atypical p-ANCA, is bound onto. The invention also provides for a means of detecting whether the said protein has actually bound with the atypical p-antineutrophil cytoplasmic antibodies.

The method for detection comprises: first obtaining a suitable bodily fluid sample, in this case since the said protein is myeloid specific, blood serum is the suitable bodily fluid. Next the bodily fluid is contacted with the said protein which is bound to the support. The bodily fluid that has not bound to the said protein should then be removed.

Once the atypical p-ANCA has bound to the 50,000 Dalton nuclear envelope protein of neutrophils and myeloid cells, the level of binding should be determined using a reproducible immunoassay technique.

This invention provides for an immunoassay technique consisting of: First, isolation of neutrophils from human peripheral blood by density gradient centrifugation (e.g., Boyum et al., 1964; Lock et al., 1994). Alternatively HL60 or 32D cells can be used. Next, this immunoassay requires preparation of cytoplasmic and crude nuclear extracts in accordance to previously published protocols outlined in Dwyer et al., 1976 and Gerace et al., 1982. SDS-Polyacrylamide Gel Electrophoresis and Immunoblotting may then be performed in accordance to Laemmli et al., 1970. This immunoassay also provides for semi-dry western blotting (Towbin et al., 1979), followed by immunodetection after preabsorption of sera containing ANCA with Human IgG in order exclude reactivity of atypical p-ANCA with IgG bound to the surface of neutrophils. Two-dimensional gel electrophoresis is then conducted in accordance to O'Farrell et al.,1975. The immunoassay then requires affinity purification of the atypical p-ANCA in accordance to Olmsted et al., 1981. Finally, this immunoassay calls for indirect immunofluorescence microscopy to detect the level of binding between the 50,000 Dalton nuclear envelope protein of neutrophils and myeloid cells, with an isoelectric point of approximately pH 6.0, and which is capable of binding with atypical p-ANCA, and atypical p-ANCA.

This invention also provides for a diagnostic kit comprising of a support where the atypical p-antineutrophil cytoplasmic antibody is bound onto. Additionally, the invention provides a means of detecting whether the said antibody has actually bound to the 50,000 Dalton nuclear envelope protein of neutrophils and myeloid cells, with an isoelectric point of approximately pH 6.0, capable of binding with atypical p-ANCA. The methods for detecting whether the said protein has bound to the said antibody on the support, as well as the methods for determination of the level of binding, may be methods outlined for prior diagnostic kits.

Experimental Details

Patients

Serum samples from 118 individuals were used in this study. Sera were obtained from patients with UC, PSC, and AIH. Serum samples from patients with Wegener granulomatosis or microscopic polyangiitis served as disease controls. Until analysis, sera were stored at −20° C. All sera were investigated for the presence of autoantibodies by indirect immunofluorescence microscopy: ANCA on ethanol-fixed neutrophils, antinuclear antibodies (ANA) on HepG2 cells, and anti-smooth muscle antibodies on rat triple liver/kidney/stomach sections. Because the aim was to detect a new target antigen recognized by atypical p-ANCA, sera containing ANCA were preferably included in this study. However, to show that a putative target antigen is uniquely recognized by atypical p-ANCA in these disorders, we also investigated a representative fraction of patients with IBD and autoimmune liver disorders whose sera did not contain ANCA. Using these selection criteria, the ANCA prevalences reported do not reflect the disease-specific frequencies of ANCA. Median serum titers of atypical p-ANCA in these patients (UC, 1:480 {n=18}; PSC, 1:1280 {n=21}; AIH, 1:12560 {n=25}) were significantly higher than those of classic p-ANCA (UC, 1:160 {n=3}; PSC, 1:640 {n=1}; AIH, 1:480 {n=2}). For the range and distribution of serum titers of atypical p-ANCA, see also FIG. 1 and Table 1. To exclude false-positive results for ANCA caused by the simultaneous presence of ANA and ANCA, the ANCA titer had to be at least 2-fold higher than the coexisting ANA titer.

Diagnoses were based on conventional clinical, radiologic, endoscopic, histologic, and serologic criteria (Truelove, et al., 1976; Johnson et al., 1993; Wiesner et al., 1989; Godman et al., 1954; Hofman et al., 1998). Disease activities in UC, PSC, and AIH were determined by established scores on the basis of clinical and laboratory data such as the Colitis Activity Index for UC (Truelove et al., 1976), Mayo Risk Score for PSC (Weisner et al., 1998), and Scoring System for the Diagnosis of Autoimmune Hepatitis (Johnson et al., 1993). Characteristics of the patients are summarized in Table 1.

TABLE 1

Characteristics of the Study Population

| Characteristics | UC | PSC | AIH | WG | mPAN | Controls[a] |
|---|---|---|---|---|---|---|
| No. of patients and controls (n = 118) | 25 | 28 | 35 | 10 | 10 | 10 |
| Sex (M/F) | 15/10 | 19/9 | 11/24 | 5/5 | 4/6 | 5/5 |
| Median age (yr) | 35 | 38 | 44 | 63 | 62 | 35 |
| Range | 9–70 | 12–70 | 16–75 | 33–79 | 39–73 | 22–56 |
| Concomitant IBD[b] | — | 14 | 0 | 0 | 0 | 0 |
| Concomitant PSC[c] | 4 | — | 12 | 0 | 0 | 0 |
| Concomitant AIH[d] | 0 | 4 | — | 0 | 0 | 0 |
| ANCA positive (titer ≧ 1:20) | 21 | 23 | 28 | 10 | 10 | 0 |
| c-ANCA | 0 | 1 | 1 | 9 | 2 | 0 |
| Classic p-ANCA | 3 | 1 | 2 | 1 | 8 | 0 |
| Atypical p-ANCA | 18 | 21 | 25 | 0 | 0 | 0 |
| Median titer of atypical p-ANCA | 1:480 | 1:1280 | 1:2560 | — | — | — |
| Range | 160–2560 | 160–5120 | 320–10,240 | | | |
| ANA positive (titer ≧ 1:80) | 3 | 6 | 15 | 2 | 0 | 0 |
| ASMA positive (titer ≧ 1:80) | 0 | 0 | 12 | 0 | 0 | 0 |
| Active/inactive disease[e] | 19/6 | 17/11 | 24/11 | 7/3 | 6/4 | 0 |
| Immunosuppressive drugs[f] | 11 | 12 | 21 | 7 | 6 | 0 |

WG, Wegener granulomatosis; mPAN, microscopic polyangiitis; ASMA, anti-smooth muscle antibodies.
[a]Controls, healthy blood donors.
[b]Patients with initial diagnosis of PSC or AIH who developed IBD during disease course.
[c]Patients with initial diagnosis of UC or AIH who developed PSC during disease course.
[d]Patients with initial diagnosis of UC or PSC who developed AIH during disease course.
[e]Active/inactive disease was assessed by established clinical scores.
[f]Corticosteroids and/or azathioprine and/or cyclosporin A.

Cells

Neutrophils were isolated from human peripheral blood of healthy donors by density gradient centrifugation (Boyum et al., 1964; Lock et al., 1994). Five milliliters of peripheral blood, anticoagulated with heparin, was carefully layered over 5.0 mL of 13.8% sodium metrizoate and 8% dextran 500 and centrifuged at 500 g for 30 minutes. After centrifugation, 2 bands became visible; the lower band contained the polymorphonuclear leukocytes. The leukocyte band was harvested and resuspended in 0.45% (wt/vol) NaCl and centrifuged at 300 g for 10 minutes. The pellet containing the neutrophils was resuspended in 0.9% NaCl and centrifuged at 500 g for 10 minutes. After repeating this washing procedure 3 times, the cell pellet was resuspended in 2 packed cell volumes of 0.9% NaCl. Vital neutrophils were counted in a Neubauer chamber using trypan blue exclusion in which viable cells do not stain with trypan blue. The neutrophil cell concentration was adjusted to $0.1 \times 10^9/L$.

Human promyelocytic leukemic HL-60 cells were grown in Iscove's modified Dulbecco's medium containing 1.5 g/L sodium bicarbonate (ATCC) supplemented with 10% (vol/vol) heat-inactivated fetal bovine serum at 37° C. and 5%

$CO_2$ in a humidified atmosphere (Collins et al., 1977; Gallagher et al., 1979). The cultures were maintained at cell densities of approximately $1\times10^6$ cells/mL. A cell passage was required every 5–7 days. Up to 50% of the HL-60 cells spontaneously differentiated to mature granulocytes that comprise banded and segmented granulocytes. To achieve differentiation rates of >90%, cells were induced by 1% (vol/vol) dimethylsulfoxide. The morphologic effects of this stimulation were noted within 4–6 days by phasecontrast microscopy showing a multilobulated nucleus ($\geq 3$ segments).

Murine myelomonocytic leukemic 32D cells were groan to a cell density of about $1\times10^6$ cells/mL (Greenberger et al., 1983). The cells were cultured in Dulbecco's modified essential medium supplemented with 10% heat-inactivated fetal bovine serum. The cells were passaged every 5–7 days. Because 32D cells are interleukin 3 dependent, sterile filtered medium of WEHI-3 cells, which produce interleukin 3 and secrete it into culture medium, was added to the 32D cell culture medium (equivalent to 1.0 ng/mL interleukin 3). WEHI-3 cells, a murine macrophagelike leukemic cell line, were obtained from ATCC and grown in Iscove's modified Dulbecco's medium (ATCC) with 0.05 mmol/L β-mercaptoethanol and 10% heat-inactivated fetal bovine serum 42. Similar to HL-60 cells, >50% of the 32D cells spontaneously differentiated to morphologically mature granulocytes. Differentiation to mature granulocytes was induced by dimethylsulfoxide, as described for HL-60 cells.

Hela cells, a human cervix cancer cell line (ATCC), were grown to confluence in Dulbecco's modified Eagle medium supplemented with 10% heat-inactivated fetal bovine serum. A cell passage was required every 3–5 days using trypsin digestion. Human hepatoblastoma liver cells (Hep G2; ATCC) were maintained in minimal essential medium, Eagle (ATCC) supplemented with 10% heat-inactivated fetal bovine serum and were grown to confluence. The culture medium was renewed every 3–5 days. Cells were detached by trypsin digestion. Monkey kidney CoS-7 cells were grown in minimal essential medium containing 10% heat-inactivated bovine serum albumin to confluence. Cells were passaged every 2–4 days using trypsin digestion.

Preparation of Cytoplasmic and Crude Nuclear Extract

Cytoplasmic and crude nuclear extracts from human neutrophils, HL-60, 32D, Hela, Hep G2, and COS-7 cells were prepared according to previously published protocols (Dwyer et al., 1976; Gerace et al., 1982). Briefly, human neutrophils from healthy blood donors were isolated by density gradient centrifugation. HL-60 and 32D suspension cells were harvested from tissue culture flasks and washed with phosphate-buffered saline (PBS). Hela, Hep G2, and Cos-7 cells were detached from the tissue culture flasks using trypsin digestion. Cells pelleted by centrifugation were resuspended in 4 packed cell volumes of hypotonic lysis buffer (10 mmol/L Tris-HCl (pH 7.5), 1 mmol/L $MgCl_2$, 1 mmol/L dithiothreitol, and 10 μmol/L phenylmethylsulfonyl fluoride) containing protease inhibitors (1 μg/mL aprotinin, bacitracin, benzamidine, leupeptin, and pepstatin) and were allowed to swell on ice for 10 minutes. Cells were disrupted with a pestle Dounce homogenizer. The cell integrity and nuclear release, respectively, were checked by phase-contrast light microscopy using an Olympus CK tissue culture inverted microscope. Lysed cells ere underlaid with a solution of 30% (wt/vol) sucrose in hypotonic lysis buffer, and the nuclei were centrifuged through the sucrose cushion at 3000 g for 20 minutes using a Beckman Centrifuge model J2-21M with a swinging-bucket rotor. The supernatant was saved as the cytoplasmic fraction. To further purify the nuclei, the pelleted nuclear fraction was resuspended in 1 packed nuclear volume of nuclear extraction buffer (20 mmol/L Tris-HCl {pH 7.5}, 0.5 mmol/L $MgCl_2$, 1 mmol/L dithiothreitol, and 10 μmol/L phenylmethylosulfonyl fluoride and protease inhibitors). The resuspended nuclear pellet was digested with 1 μmg/mL deoxyribonuclease (DNAse) I and 10 μg/mL ribonuclease (RNAse) A for 15 minutes at room temperature to separate the nuclear envelope from the nucleoplasmic and DNA-adherent proteins. The nuclear fragments were then pelleted by centrifugation at 14,000 g for 20 seconds. To remove anchoring cytoplasmic proteins, the nuclear envelope fraction was washed 5 times with 1 packed nuclear volume of nuclear extraction buffer containing 500 mmol/L NaCl. The supernatants of the salt-washes were saved and pooled. Finally, the nuclear envelope fraction was washed 5 times in nuclear extraction buffer and sonicated for 5 seconds with a model 6 Sonic Dismembrator to solubilize the nuclear lamina and nuclear membranes. Each subcellular fraction was diluted 1:1 with sample buffer (250 mmol/L Tris-HCl {pH 6.8}, 4% {wt/vol} sodium dodecyl sulfate {SDS}, 0.005% {wt/vol}bromphenol blue, 20% {vol/vol} glycerol, and 5% {vol/vol} β-mercaptoethanol). The samples were stored at −20° C. To determine the protein concentration of each subcellular fraction, equal aliquots of each sample and of bovine serum albumin standards were dotted onto nitrocellulose and stained with Ponceau S.

Detailed Preparation of Cell Extracts from HL-60 Cells

Human HL-60 suspension cells were harvested from tissue culture flasks and washed once with phosphate buffered saline (PBS). The cells were pelleted by centrifugation at 3000 rpmi for 10 minutes at 21 degrees Centigrade. To swell the cells, the cells were resuspended in four packed cell volumes of hyptonic lysis buffer (10 mM TrisHCL, pH 7.5; 1 mM $MgCl_2$) containing 10% (w/v) sucrose, 1 mM dithiothreitol, 10 μM phenylmethylsulfonyl fluoride and protease inhibitors (1 μg/ml of aprotinin, bacitracin, benzamidine, leupeptin, pepstatin for 20 minutes on ice. The pelleted cells (3000 rpmi, 5 minutes at 4 degrees Centigrade) were resuspended in four packed cell volumes of hypotonic lysis buffer containing 1% (v/v) Triton-X 100. After centrifugation (3000 rpmi, 5 minutes at 4 degrees Centigrade), the cells were disrupted with a pestle dounce homogenizer (40 times per 1 mL of cell suspension). The cell integrity and the nuclear release, respectively were checked by phase contrast light microscopy using an Olympus CK tissue culture inverted microscope. To remove adherent bulks of cytokeratins and other cytoplasmic proteins from the nuclei, the cell suspension was incubated with 2 mM vanadyl ribonucleoside complex with occasional vortexing for ten minutes on ice. The suspension of the lysed cells was laid on top of a sucrose gradient (2.2M/1.1 M sucrose in hypotonic lysis buffer). The nuclei were pelleted through the sucrose cushion by ultracentrifugation (28,000 rpmi, 4 degrees centigrade for 60 minutes). The pelleted nuclei were resuspended in one packed volume of nuclear extraction buffer 920 mM trisHCl, pH 7.5; 0.5 mM $MgCl_2$) containing 0.5% (v/v) Triton X-100, 1 mM dithiothreitol, 10 μM phenylmethylsulfonyl fluoride and protease inhibitors (1 μg/mL of aprotinin, bactracin, benzamidine, leupeptin, pepstatin) and were digested with 1 μg/mL DNAse I and 10 μg/mL RNAse A for fifteen minutes at room temperature to separate the nuclear envelope from the nucleoplasmic and DNA-adherent proteins. The nuclear envelope fragments were pelleted by centrifugation at 13,000 g for twenty seconds at room temperature. To remove anchoring cytoplasmic proteins, the pellet consisting of the nuclear envelope proteins were resuspended in one packed nuclear volume of 500 mM NaCl and pelleted again (13000 g, 20 seconds, at room temperature). The salt washes were repeated five times. The supernatants of the salt washes were saved and pooled. To remove the sodium chloride, the nuclear envelope fraction was washed five times with nuclear extraction buffer. An ultrasonicator was used to solubilize the nuclear lamina and the nuclear membranes. The nuclear envelope fraction was diluted 1:1 with sample buffer (250 mM TrisHCl, pH 6.8; 4% w/v) sodium dodecyl sulfate; 0.005% (w/v) Bromphenol blue; 20% (v/v) glycerol; 5% (v/v) β-mercaptoethanol). The samples were stored at −20 degrees centigrade.

To determine the protein concentration of the nuclear envelope fraction, equal aliquots of the subcellular fraction and the bovine serum albumin standards (10 mg/mL, 5 mg/mL, 1 mg/mL, 0.5 mg/mL, 0.1 mg/mL) were dotted onto a nitrocellulose membrane and stained with Ponceau S.

The nuclear cell extracts were resolved using SDS-polyacrylamide gel electrophoresis under reducing conditions according to standard protocols (Laemmli et al., 1970). To achieve best separation of the nuclear proteins, 4–20% gradient gels were used. Protein bands were stained with Coomassie blue solution (0.05%(w/v)) Coomassie brilliant blue R, and 50% (v/v) methanol.

After SDS-PAGE, the resolved proteins were transformed onto a nitrocellulose membrane by semi-dry Western blotting (Towbin et al., 1979). To detect reactive proteins, the nitrocellulose membrane was probed with sera, diluted 1:5,000 to 1:10,000 in blocking solution (2% (w/v) bovine serum albumin in PBS and 0.01% (v/v) Tween-20 for one hour at room temperature). After extensive washing with PBS and 0.01% Tween-20, the proteins reacting with ANCA were detected by horseradish peroxidase conjugated sheep anti-human lgG (H+L) secondary antibodies, diluted 1:10,000–1:20,000 and visualized by enhanced chemiluminescence using ECL Western blotting detection reagents. The nitrocellulose membrane was exposed to a Hyperfilm ECL in the dark for 10–60 seconds.

SDS-Polyacrylamide Gel Electrophoresis and Immunoblotting

SDS-polyacrylamide gel electrophoresis (SDS-PAGE) under reducing conditions was performed according to standard protocols (Laemmli et al., 1970). Samples containing equal amounts of proteins were resuspended in sample buffer and resolved on 4%–20% gradient gels (Bio-Rad, Hercules, Calif.). Proteins were stained with Coomassie blue solution (0.05% {wt/vol} Coomassie brilliant blue R {Sigma}, 50% {vol/vol} methanol, and 10% {vol/vol} acetic acid) or were detected by silver nitrate staining.

Semidry Western blotting was performed according to Towbin et al. After SDS-Page, the resolved proteins were transferred onto a nitrocellulose membrane. For detection of reactive proteins, the nitrocellulose membrane was probed with sera, diluted 1:5000 to 1:10,000 in blocking solution (2% wt/vol) bovine serum albumin in PBS and 0.01% (vol/vol) Tween-20, or polyclonal rabbit antibodies to human IgG, diluted 1:1000, for 1 hour at room temperature. After several washing steps with PBS and 0.01% Tween-20, the resolved proteins reacting with ANCA were detected by horseradish peroxidase-conjugated sheep anti-human IgG (H+L) secondary antibodies (diluted 1:10,000 to 1:20,000;, and visualized by enhanced chemiluminescence using enhanced chemiluminescence (ECL) Western blotting detection reagents. The nitrocellulose membrane was exposed to a Hyperfilm ECL in the dark for 10–60 seconds. The blots were scanned with an Epson Expression 636 Scanner, and the mean signal densities of reactive bands and the background of the blots, given as arbitrary units±SD, were calculated with National Institutes of Health (NIH) Image version 1.61 software downloaded from the NIH website.

Immunodetection After Preabsorption of Sera Containing ANCA with Human IgG

To exclude reactivity of atypical p-ANCA with IgG bound to the surface of neutrophils via Fc receptor, a representative portion of sera (UC, n=5; PSC, n=5; AIH, n=6; Wegener granulomatosis, n=3; microscopic polyangiitis, n=3) was preabsorbed with human IgG (H+L). IgG was added to each patient's serum at serial dilutions (1:200 to 1:2000) and incubated for 30 minutes at 37° C. After centrifugation at 15,000 g for 30 minutes, the supernatant was used for immunodetection of reactive proteins from nuclear myeloid cell extracts. Immunodetection was performed as described above.

Two-Dimensional Gel Electrophoresis

Two-dimensional gel electrophoresis was performed according to standard protocols (O'Farrell et al., 1975). Briefly, isoelectric focusing gels were cast in glass tubings using a degassed solution of 9.2 mol/L urea; 4% (wt/vol) bis-/acrylamide (Bio-Rad); 20% (vol/vol) Triton X-100; 1.6% (vol/vol) ampholytes (pH 5–7; Bio-Rad); 0.4% (vol/vol) ampholytes (pH 3–10; Bio-Rad); 0.01% (wt/vol) ammonium persulfate; and 0.1% (wt/vol) N,N,N',N'-tetramethylenediamine. Gels were placed in a Hoefer Series 600 electrophoresis apparatus; the lower reservoir contained 10 mmol/L orthophosphoric acid, and the upper reservoir was filled with degassed 20 mmol/L NaOH. The gels were pre-electrophoresed at 200 V for 15 minutes, 300 V for 30 minutes, and 400 V for 30 minutes. The samples were resuspended in sample buffer (9.5 mol/L urea, 20% Triton X-100, 5% β-mercaptoethanol, 1.6% ampholytes {pH 5–7}, and 0.4% ampholytes {pH 3–10}). Equal amounts of the samples were loaded onto the gels. The samples were resolved at 400 V for 12–15 hours and at 800 V for 1 hour.

The isoelectric focusing was followed by SDS-PAGE as described above. The gels were extruded and equilibrated with SDS equilibration buffer (0.0625 mol/L Tris-HCI {pH 6.8}, 2.3% SDS, 5.0% β-mercaptoethanol, 10% glycerol, and 0.001% bromphenol blue) for 10 minutes. The isoelectric focusing gels were loaded onto a 12.5% separation gel and electrophoresed together with molecular mass standards at 200 V for 6 hours. Staining and/or immunoblotting of the 2-dimensional gel was performed as described above.

Affinity-Purification of Atypical p-ANCA

Antibodies were affinity-purified from sera using previously described methods (Olmsted et al., 1981; Smith D E et al., 1984). Briefly, proteins of the nuclear extracts from HL-60 or 32D cells were resolved by SDS-PAGE and transferred onto a nitrocellulose membrane by semidry Western blotting. Reactive band(s) were detected by incubation with sera containing atypical p-ANCA and were visualized by enhanced chemiluminescence. A strip of the nitrocellulose membrane containing the protein of interest and the bound antibodies was cut out from the nitrocellulose membrane by using the developed film to align the reactive band. The antibodies were eluted by incubation with 200 mmol/L glycine (pH 2.8) and 1 mmol/L EDTA for 20 seconds. The elution process was repeated 3 times for each sample, and the aliquots were combined. The acid elution buffer was neutralized by adding 50–100 µL of 1 mol/L Tris base. Affinity-purified antibodies were diluted 1:80 in PBS for use in immunofluorescence in microscopy. For immunoblotting experiments, the affinity-purified antibodies were diluted 1:10,000 in sample buffer.

Indirect Immunofluorescence Microscopy

Indirect immunofluorescence microscopy was performed to determine the fluorescence pattern produced by each sample (Wiik et al., 1989). Briefly, slides with ethanol-fixed neutrophils, HL-60, 32D, Hela, Hep G2, and COS-7 cells were incubated with serum samples, diluted 1:20, in a humidified chamber at room temperature for 30 minutes. After extensive washes with PBS, bound antibodies were detected with fluorescein isothiocyanate (FITC)-conjugated goat anti-human IgG (H+L) secondary antibodies at room temperature for 20 minutes followed by 2 further washing steps. After mounting with an antifading medium, slides were viewed with an inverted Zeiss Axiovvert 100 TV fluorescence microscope with 60× and 100× oil immersion objectives. To determine the ANCA titer, serial 2-fold dilutions of sera were made up to the highest dilution, which still gave a characteristic ANCA fluorescence pattern on ethanol-fixed neutrophils. ANCA titers>1:20 were considered positive.

To evaluate if the target protein recognized by atypical p-ANCA is adherent to DNA, ethanol-fixed myeloid cells were preincubated with DNAse I at a concentration of 3 IU/mL for 30 minutes at 37° C. After extensive washing of the slides with PBS, the slides were processed for indirect immunofluorescence microscopy as described above. A representative portion of sera (UC, n=5; AiH, n=5) was investigated.

For double-labeling immunofluorescence microscopy, sera containing atypical p-ANCA (diluted 1:20 in PBS) and antibodies against nuclear envelope proteins such as rabbit lamin B1 (Cance et al., 1992) or rabbit lamin B receptor (Collas et al., 1996) (diluted 1:100) were incubated on the cell slides at room temperature for 30 minutes. Antibodies to nuclear envelope proteins were visualized by Texas red-conjugated goat anti-rabbit IgG (H+L) secondary antibodies (diluted 1:200; Jackson ImmunoResearch). ANCA detection with FITC-conjugated secondary antibodies was performed as described above. The slides were examined by confocal laser scanning microscopy using a Zeiss CSM 410 confocal laser scanning system attached to an inverted Zeiss Axiovert 100 TV fluorescence microscope and equipped with a 100× objective. Horizontal optical sectioning of the cells was performed in 1-μm steps. Photographs of the ANCA fluorescence patterns, detected by FITC-conjugated secondary antibodies taken at 525-nm wavelength, were optically superimposed with images of antibodies against lamin B1 or the lamin B receptor detected by Texas red-labeled secondary antibodies taken at 570-nm wavelength. Colocalization was identified by a yellow staining that resulted from the mixed color of the green signal from FITC-labeled secondary antibodies and the red signal of Texas red-conjugated secondary antibodies. Images were processed using Photoshop version 4.0 software on a Macintosh Apple G3 computer.

Results

Figure 2B:
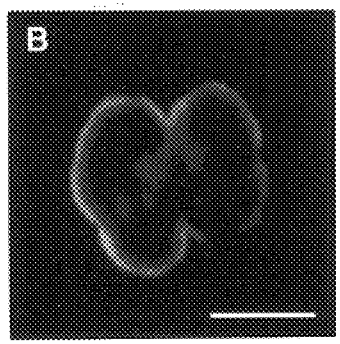
Figure 2C:
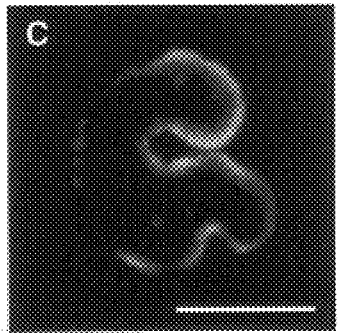
Figure 2D:
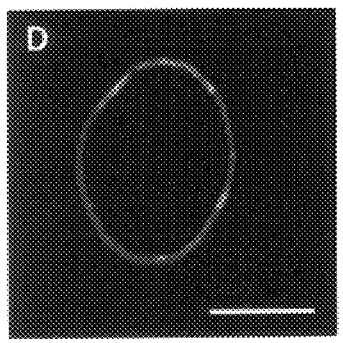
Figure 2E:
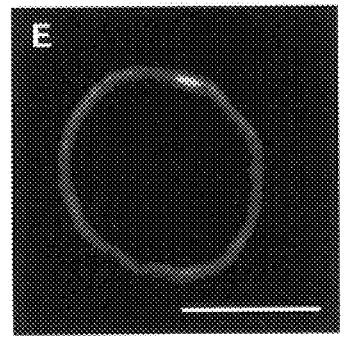
Figure 2F:
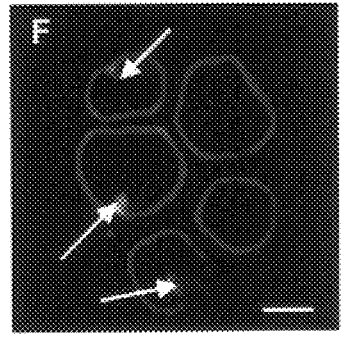
Figure 2G:
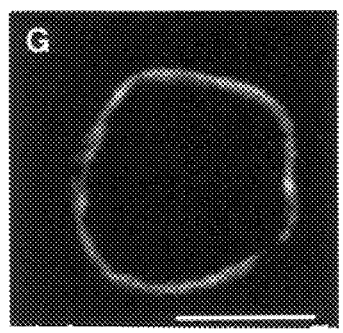
Figure 2H:
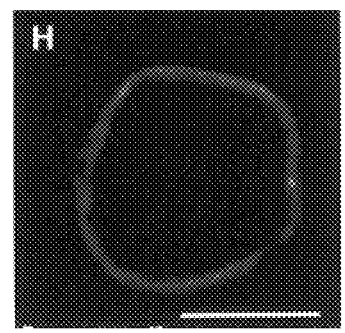
Figure 2I:
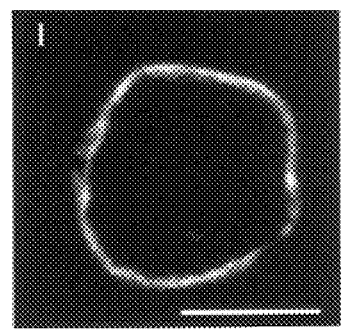

Microscopic Immunofluorescence Patterns of Atypical p-ANCA on HL-60 and 32D Cells Staining patterns of ANCA on ethanol-fixed neutrophils, assessed by indirect immunofluorescence microscopy, are well-characterized. However, labeling of human promyelocytic leukemic HL-60 cells and murine myelomonocytic leukemic 32D cells with ANCA has not been systematically studied, particularly for atypical p-ANCA. HL-60 and 32D cells are both of the myeloid lineage and can be differentiated to mature granulocytes by treatment with dimenthyl-sulfoxide. When examined by confocal laser scanning microscopy, all sera containing atypical p-ANCA (n=64/64) showed a similar fluorescence pattern on ethanol-fixed differentiated HL-60 and 32D cells compared with ethanol-fixed neutrophils. This fluorescence pattern was characterized by a broad inhomogeneous staining of the nuclear periphery along with scattered intranuclear fluorescent foci (FIGS. 2A–C). Only a rim-like staining of the nuclear periphery was seen on undifferentiated HL-60 and 32D cells whose nuclei were not segmented. Therefore, the characteristic intranucear fluorescent foci of atypical p-ANCA, likely corresponding to infoldings of the multilobulated neutrophilic nucleus, were not observed on these undifferentiated cells (FIGS. 2D–F). The FITC fluorescence signal revealing atypical p-ANCA completely colocalized with the Texas red-fluorescence signal used to detect antibodies against lamin B1 or lamin B receptor (FIGS. 2G–I). Pretreatment of neutrophils with DNAse did not alter the fluorescence pattern of the atypical p-ANCA on ethanol-fixed myeloid cells. The c-ANCA fluorescence patterns found in sera from all patients with Wegener granulomatosis (n=9/10), as well as the "classic p-ANCA" staining detected in sera from patients with microscopic polyangitis (n=8/10), did not significantly differ in their labeling characteristics on ethanol-fixed HL-60 and 32D cells compared with the well-known staining patterns on ethanol-fixed neutrophils (data not shown).

Figure 3A:
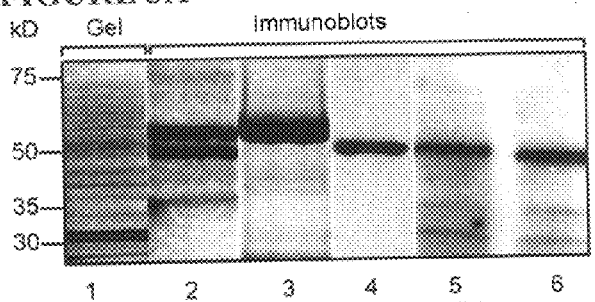
FIG. 3: Immunoblots showing reactivity of ANCA with nuclear proteins of HL-60 cell extracts. (A) Proteins of neutrophil or HL-60 nuclear cell extracts were resolved by SDS-PAGE on 4%–20% gradient gels and immunoblotted with atypical p-ANCA. Lane 1: A nuclear cell extract of neutrophils electrophoresed and stained with Coomassie blue. Lane 2: Immunoblots of nuclear extracts showing 2 reactive proteins at 50/53 kilodaltons after incubation with serum from a PCS patient with atypical p-ANCA. Lane 3: The 53-kilodalton protein reacted with antibodies to human lgG (H+L). Lane 4: After preabsorption of the serum used in lane 2 with human lgG (H+L), the 53-kilodalton protein was not detected. The results in lanes 3 and 4 confirmed the 53-kilodalton protein as the heavy chain of lgG. Lane 5 and 6: The reactivity with the heavy chain of lgG (lane 3) was no longer detectable when the HL-60 and 32D nuclear cell extracts were immunoblotted with the same serum as in lane 2. Reactivity was only found with the 50-kilodalton nuclear envelope protein. (B) Nuclear (NE) and cytoplasmic (cyt) extracts of HL-60 cells were electrophoretically resolved and immunoblotted with various sera containing ANCA. Sera from patients with AIH (lanes 1 and 2), PSC (lanes 3 and 4), and UC (lanes 5 and 6). The serum of a patient with Wegener granulomatosis and c-ANCA (lanes 7 and 8) did not show any specific reactivity with nuclear proteins of HL-60 cells, whereas the serum specifically reacted with a 29-kilodalton cytoplasmic protein, corresponding to proteinase 3. No reactivity to any nuclear protein of HL-60 cells extracts was found after immunoblotting with the sera from patients with UC, PSC, or AIH that did not contain ANCA (lanes 9–11) or from healthy blood donors without detectable ANCA (lane 12). Migrations of molecular mass standards in kilodaltons are indicated at the left of each panel. Sera were diluted 1:5000 to 1:10,000 for use in immunoblotting.
Figure 3B:
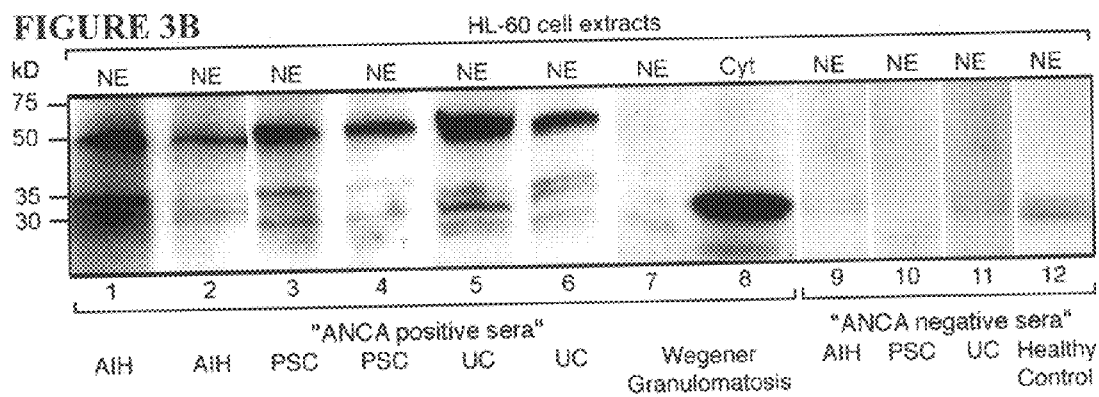

Identification of a Nuclear Envelope Protein as the Predominant Target Antigen of Atypical p-ANCA In immunoblotting experiments with nuclear envelope extracts of neutrophils, 92% (n=59/64) of the sera with atypical p-ANCA (UC, n=16/18; PSC, n=20/21; AIH, n=23/25) reacted with nuclear proteins at apparent molecular masses of 50 and 53 kilodaltons. However, because the reactive 53-kilodalton protein was detected on immunoblots of cytoplasmic as well as of nuclear cell extracts, nonspecific reactivity is highly suspicious in the labeling of this 53-kilodalton protein. By using antibodies to human IgG (H+L) and by preabsorbing sera containing ANCA with human IgG (H+L), the 53-kilodalton protein was identified as the heavy chain of IgG (FIG. 3A). This nonspecific reactivity of the 53-kilodalton protein with atypical p-ANCA was likely a result of the facts that atypical p-ANCA nonspecifically interact with IgG bound to the surface of neutrophils via Fc receptor and that neutrophils, separated from peripheral blood, are frequently contaminated with IgG-producing B lymphocytes. To test this hypothesis, nuclear extracts of HL-60 and 32D cells that do not have an IgG receptor on their cell surface were examined. None of the sera containing atypical p-ANCA reacted with a 53-kilodalton protein in HL-60 and 32D nuclear extracts, but 92% of the sera reacted with the 50-kilodalton nuclear envelope protein (FIG. 3B). No correlation between the endpoint serum titer of the ANCA and the mean signal intensity of the 50-kilodalton nuclear envelope protein on scanned immunoblots, (median serum titer of atypical p-ANCA, 1:1280; mean signal intensity of the 50-kilodalton nuclear envelope protein on scanned immunoblots, 78.55±8.84 arbitrary units; P=0.97 {NS}) could be found. In addition, none of the sera without detectable ANCA recognized the 50-kilodalton nuclear protein (FIG. 3B).

Figure 4A:
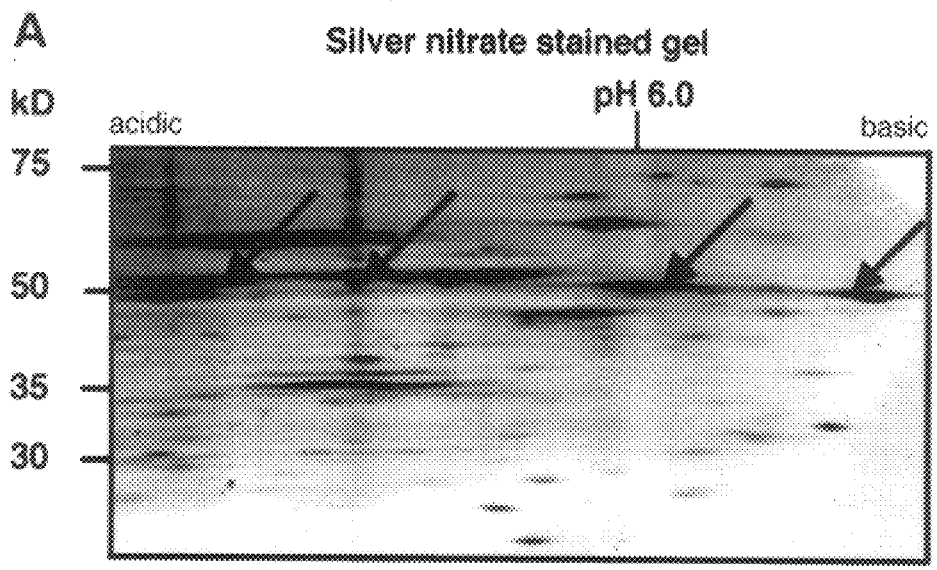
FIG. 4: Two-dimensional gel electrophoresis of nuclear HL-60 cell extracts and immunoblotting with atypical p-ANCA. Proteins were separated in the first dimension by isoelectric focusing and in the second dimension by SDS-PAGE. (A) Proteins of a nuclear HL-60 cell extract, resolved by 2-dimensional gel electrophoresis, were stained by silver nitrate. The apparently unique nuclear envelope protein of 50 kilodaltons identified by 1-dimensional gel electrophoresis was resolved into multiple proteins with the same apparent molecular masses, but different isoelectric points (arrows). (B) After immunoblotting of the 2-dimensional gel, a nuclear protein recognized by atypical p-ANCA was detected at 50 kilodaltons with an isoelectric point of approximately pH 6.0 (arrows). Migrations of molecular mass standards in kilodaltons are indicated at the left.
Figure 4B:
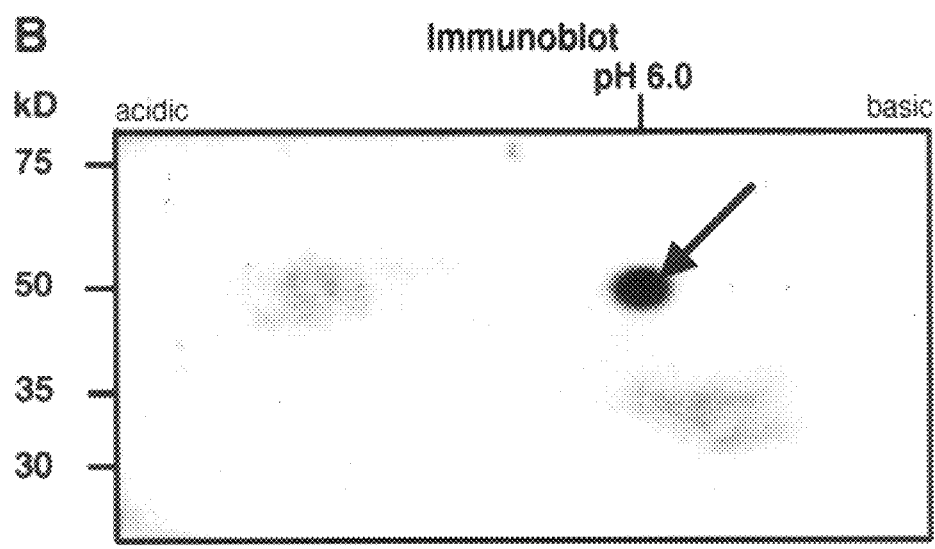
Figure 5A:
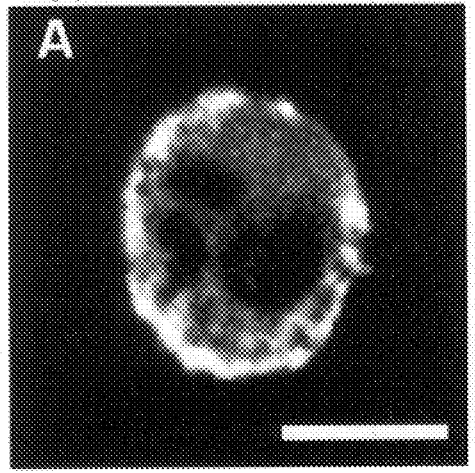
FIG. 5: Microscopic immunofluorescence patterns of sera containing atypical p-ANCA and simultaneously present antibodies to other nuclear proteins before and after affinity-purification of atypical p-ANCA. Typical p-ANCA and ANA were detected with FITC-conjugated goat anti-human lgG secondary antibodies on ethanol-fixed HL-60 cells. The fluorescence patterns were visualized by confocal laser scanning microscopy. (A) Serum from an AIH patient showing rim-like peripheral nuclear fluorescence caused by atypical p-ANCA along with a homogeneous nuclear staining caused by ANA of a different specificity. (B) After affinity-purification of the sera against the identified 50-kilodalton nuclear envelope protein, the homogeneous intranuclear staining disappeared. (C) Rim-like peripheral nuclear fluorescence caused by the presence of atypical p-ANCA together with speckled intranuclear staining caused by ANA was detected in another patient with AIH. (D) Only peripheral rim-like nuclear staining remained after affinity-purification of atypical p-ANCA against the 50-kilodalton nuclear envelope protein. Bars=10 $\mu$m. For use in immunofluorescence microscopy, nonaffinity-purified sera were diluted 1:20, and affinity-purified antibodies were diluted 1:80.
Figure 5B:
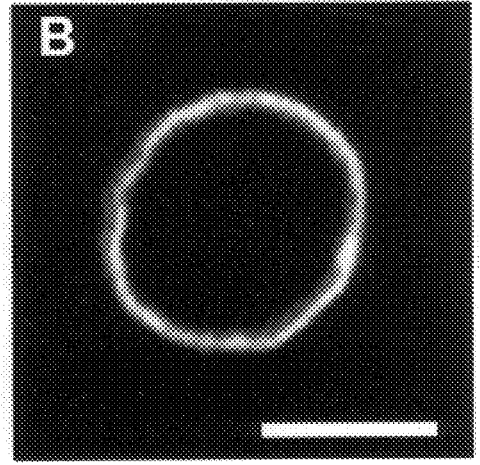
Figure 5C:
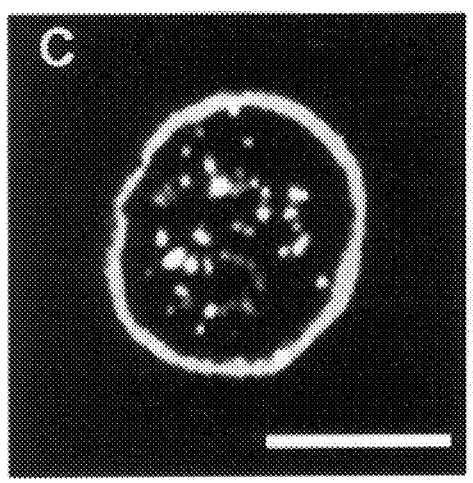
Figure 5D:
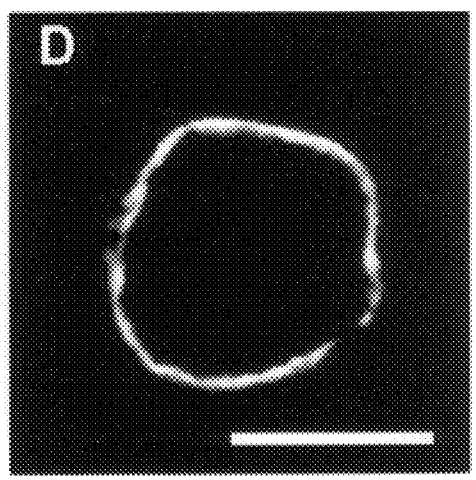

Using 2-dimensional gel electrophoresis, the apparently unique nuclear envelope protein 50 kilodaltons identified by 1-dimensional gel electrophoresis was separated into multiple proteins with the same apparent molecular mass, but different isoelectric points (FIG. 4A). Proteins of nuclear HL-60 and 32D extracts, separated by 2-dimensional gel electrophoresis, were immunoblotted with sera containing atypical p-ANCA. A 50-kilodalton nuclear envelope protein with an isoelectric point of approximately pH 6.0 was identified (FIG. 4B). These observations show that the predominant antigen recognized by the majority of atypical p-ANCA is a 50-kilodalton nuclear envelope protein with an isoelectric point of approximately pH 6.0.

Affinity-Purification of Atypical p-ANCA

Antibodies were affinity-purified from sera against the 50-kilodalton nuclear envelope protein of HL-60 and 32D cell extracts. When these affinity-purified antibodies were investigated for their staining characteristics on either ethanol-fixed neutrophils, HL-60, or 32D cells by indirect immunofluorescence microscopy, the purified antibodies gave a similar rim-like peripheral nuclear fluorescence pattern as seen with nonpurified atypical p-ANCA. However, atypical p-ANCA and antibodies to other nuclear antigens (ANA) are often simultaneously present in sera from patients with UC, PSC, and especially AIH. In the sample population used, 31% (n=20/64) of the sera simultaneously contained atypical p-ANCA and ANA. On ethanol-fixed neutrophils, these particular sera showed a rim-like peripheral nuclear fluorescence caused by atypical p-ANCA along with a homogeneous or speckled nuclear staining caused by ANA. When atypical p-ANCA were affinity-purified from sera against the 50-kilodalton nuclear envelope protein, the homogeneous or speckled intranuclear staining caused by the presence of antibodies against other nuclear proteins than the 50-kilodalton one disappeared (FIG. 5). The fluorescence pattern of affinity-purified atypical p-ANCA was identical with the fluorescence labeling of antibodies to nuclear envelope proteins (FIGS. 6A–C). On immunoblots of nuclear extracts from HL-60 and 32D cells incubated with sera containing atypical p-ANCA, two further reactive nuclear proteins with apparent molecular masses of 30 and 35 kilodaltons were detected besides the 50-kilodalton nuclear protein. However, these two nuclear proteins produced a signaificantly lower mean signal intensity on scanned immunoblots than the 50-kilodalton nuclear protein (24.02±6.77 and 15.58±7.9 arbitrary units vs. 78.55±8.84 arbitrary units; p<0.05). Antibodies affinity-purified from sera against the 30- and 35-kilodalton nuclear proteins did not yield any specific fluorescence signal on any of the examined cell lines (FIGS. 6D–E).

Myeloid Cell-Specific Reactivity of the 50-Kilodalton Nuclear Envelope Protein

Figure 7A:
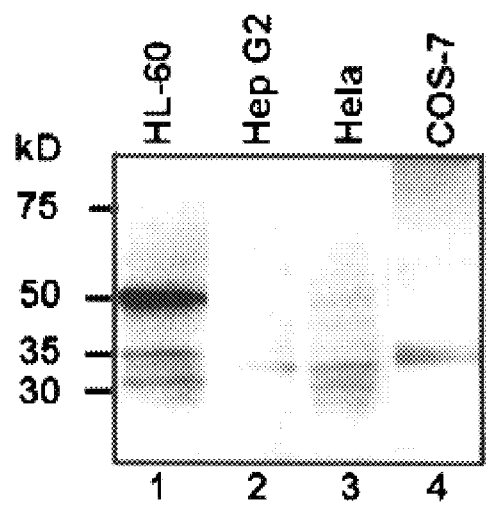
FIG. 7: Myeloid cell-specific reactivity of affinity-purified atypical p-ANCA. (A) Nuclear extracts of HL-60, Hep G2, Hela, and COS-7 cells were electrophoretically resolved and immunoblotted with atypical p-ANCA affinity-purified against the 50-kilodalton nuclear envelope protein (diluted 1:2). Lane 1: Affinity-purified atypical p-ANCA reacted with a 50-kilodalton nuclear target protein of HL-60 cell extracts. Lane 2–4: No specific reactivity of affinity-purified atypical p-ANCA was found with nuclear proteins of Hep G2, Hela, and COS-7 cells. Migration of molecular mass standards is indicated in kilodaltons on the left. (B–E) Confocal laser scanning microscopy was used to evaluate the labeling obtained by affinity-purified atypical p-ANCA on ethanol-fixed HL-60, Hep G2, Hela, and COS-7 cells (diluted 1:4). For each cell type, we used the same serum sample from a patient with AIH, containing antibodies affinity-purified against the 50-kilodalton nuclear envelope protein. The affinity-purified atypical p-ANCA were detected with FITC-conjugated goat antihuman IgG secondary antibodies. On HL-60 cells, the affinity-purified atypical gave the characteristic peripheral rim-like nuclear fluorescence together with multiple intranuclear fluorescent foci, as observed with neutrophils (B). Only a nonspecific background staining after incubation with affinity-purified atypical p-ANCA was detected using Hep G2 (C), Hela (D), and COS 7 cells (E). Bars=10 μm.
Figure 7B:
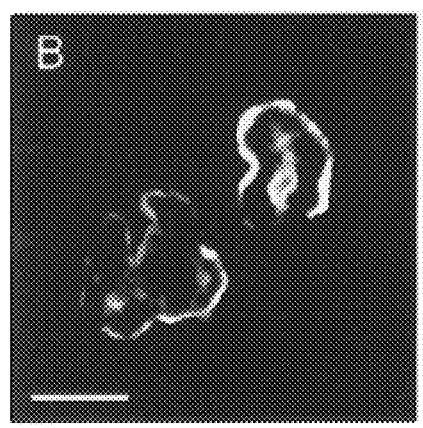
Figure 7C:
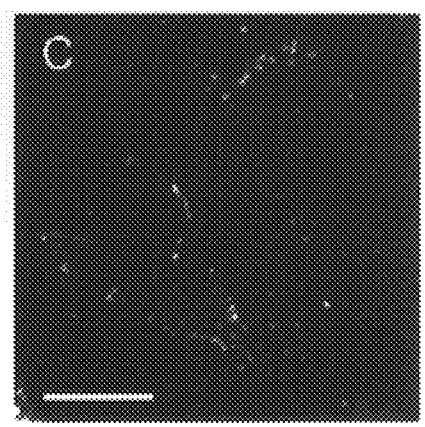
Figure 7D:
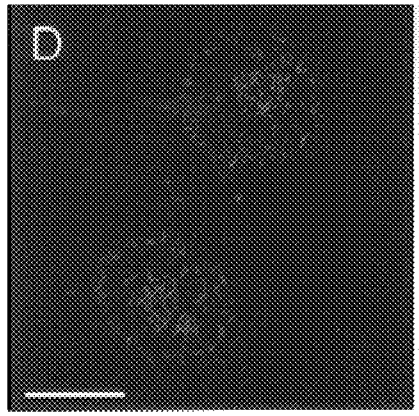
Figure 7E:
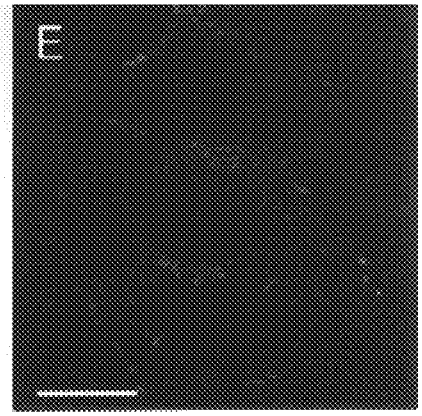

Reactivity of atypical p-ANCA to the 50-kilodalton nuclear envelope protein was confined to myeloid cells such as human neutrophils, HL-60, or 32D cells. Affinity-purified atypical p-ANCA did not react with electrophoretically resolved nuclear envelope proteins of Hep G2, Hela, and COS-7 cells in immunoblotting experiments (FIG. 7A). In addition, these antibodies only gave a nonspecific fluorescence labeling on Hep G2, Hela, and COS-7 cells (FIG. 7B). Hence, the 50-kilodalton nuclear envelope protein recognized by atypical p-ANCA is myeloid cell specific.

Discussion

Putative cytoplasmic target antigens of a typical p-ANCA in IBD and autoimmune liver disease have been previously studied (Stoffel et al., 1996; Walmsley et al., 1997; Keilner et al., 1998; Roozendaal et al., 1998; Halbwachs-Mecarelli et al., 1992; Peen et al., 1993). However, only a minority of sera (20%–35%) reportedly reacted with these cytoplasmic proteins. In light of recent data showing that the target antigen of a typical p-ANCA colocalizes with proteins of the nuclear envelope of neutrophils(Terjung et al., 1998), the present method aimed to further characterize a nuclear target protein of a typical p-ANCA. It may now be reported that a 50-kilodalton nuclear envelope protein with an isoelectric point of pH 6.0 was recognized by more than 90% of a typical p-ANCA in individual with IBD, PSC, and AIH. c-ANCA and classic p-ANCA did not react with this protein. Previous efforts reported by other groups to identify a cytoplasmic target antigen of a typical p-ANCA resulted from consistent interpretation of the term "antineutrophil cytoplasmic antibodies" (ANCA) As a consequence of this term, cytoplasmic fractions were exclusively used as antigenic substrate for experimental approaches to further characterize the target protein. The additional preparation of specific nuclear cell extracts from myeloid cells were essential. As a result, the term a typical p-ANCA should be considered as a misnomer and replaced by the more appropriate term "antineutrophil nuclear antibodies" (ANNA).

The subcellular localization of the 50-kilodalton nuclear target antigen of atypical p-ANCA could be assigned to the nuclear envelope of myeloid cells. Atypical p-ANCA that were affinity purified against the 50 kilodalton nuclear envelope protein showed an identical fluorescence pattern, as observed with antibodies to nuclear envelope proteins such as lamin B1 and the lamin B receptor. In higher mammalian somatic cells, lamins and the lamin B receptor (Worman et al., 1988; Worman et al., 1990) are protein components of the nuclear envelope. The nuclear envelope consists of the outer and inner nuclear membranes, the nuclear pore complexes, and the nuclear lamina, a meshwork of intermediate filaments which is adjacent to the inner nuclear membrane and to a portion of the interphase heterochromatin (Courvalin et al., 1990; Courvalin et al., 1991; Worman et al., 1991; Bartin et al., 1998. Various nuclear envelope proteins have been reported as target antigens of autoantibodies in autoimmuneliver disorders in varying prevalences. Antibodies to lamins A, C, and B1 are found in patients with AIH (Lassoued et al., 1988; Wesierska-Gadek et al., 1988). Approximately 25% of individuals with primary biliary cirrhosis have autoantibodies that recognize a nuclear pore complex protein gp210 (Courvalin et al., 1990; Lassoued et al., 1990). Less frequently, individuals with primary biliary cirrhosis have antibodies against lamin B receptor (Courvalin et al., 1990; Nickowitz et al., 1994; Lin et al., 1996). In patients with PSC or IBD, the prevalence of antibodies to nuclear envelope proteins has not been systematically studied. As the identification of new nuclear envelope proteins progresses, subsequent studies may identify additional patients with autoimmune liver disorders producing autoantibodies against various nuclear envelope proteins. The 50-kilodalton myeloid-specific nuclear envelope protein recognized by 92% of atypical p-ANCA in IBD and autoimmune liver disease represents an example.

Reactivity to the 50-kilodalton nuclear envelope protein recognized by atypical p-ANCA was confined to myeloid cells. The myeloid cell-specific expression of this nuclear envelope protein goes along with part of the definition of "ANCA" being autoantibody directed against constituents of neutrophils. Various target antigens of atypical p-ANCA suggested by other groups, such as catalase (Kelner et al., 1998; Roozendaal et al., 1998), enlase (Kelner et al., 1998; Roozendaal et al., 1998), histone H1 (Eggena et al., 1996; Cohavy et al., 1997; Cohavy et al., 1998), or high-mobility group nonhistone chromosomal proteins (Sobajima et al., 1997; Sobajima et al., 1999) are not uniquely present in neutrophils or other myeloid cells, but are found in most higher eukaryotic somatic cells. However, these investigations suggest that specific epitopes of these proteins recognized by atypical p-ANCA may be unique or only immunoaccessible in neutrophils (Cohavy et al., 1997; Cohavy et al., 1998). The present immunoblotting and immunofluorescence microscopy data clearly indicate that the reactivity of atypical p-ANCA with-the 50-kilodalton nuclear envelope protein was only seen in myeloid cells. If present in other somatic cells than myeloid cells, the target protein would be at a level below detectability by immunoblotting and immunofluoresence microscopy.

In addition to identifying a nuclear target antigen of atypical p-ANCA, it seems that myelomonocytic leukemic HL-60 and 32D cells are well suited for the detection of these autoantibodies. The fluorescence pattern of classic p-ANCA and c-ANCA observed by immunofluorescence microscopy on ethanol fixed HL-60 cells were very similar to those reported for ethanol fixed neutrophils.

Moreover, it is also shown that the staining characteristics of a typical p-ANCA on neutrophilic granulocytes were indistinguishable from those on HL-60 or 32D cells. These two tumor cell lines are easy to maintain in large quantities, rendering them particularly suitable substrates for studying ANCA. Contrary to the time-consuming separation of neutrophils from human peripheral blood, no handling of potentially infectious blood products is invloved when HL-60 and 32D cells are used. Compared with neutrophils, these two cell lines do not express IgG receptors on their cell surface, nor are they contaminated by Ig producing B lymphocytes. Therefore, contamination by the heavy and light chains of IgG, observed when neutrophils are used, does not interfere with the interpretation of immunoblotting results.

Although HL-60 and 32D cells can be differentiated easily into morphologically mature granulocytes, this differentiation process is not mandatory when these cell lines are used for immunofluorescence microscopy studies or immunoblotting of cell extracts in the detection of atypical p-ANCA. The fluorescence pattern of atypical p-ANCA on ethanol fixed HL-60 and 32D cells, irrespective of being undifferentiated or differentiated, was comparable with the characteristic rim-like nuclear staining pattern on ethanol fixed neutrophils. This observation indicates that the nuclear target antigen is already present and immunoaccessible in undifferentiated HL-60 and 32D cells. However, unless high resolution microscopy, such as confocal laser scanning microscopy is used, it is recommended to induce differentiation of the HL-60 and 32D cells to reliable distinguish atypical p-ANCA from classic p-ANCA staining. The latter lacks the scattered intranuclear fluorescent foci resulting from labeling of nuclear envelope invaginations that were regularly seen with atypical p-ANCA staining on neutrophils or differentiated HL-60 and 32D cells.

Molecular identification of the 50-kilodalton nuclear target antigen of atypical p-ANCA, or more precisely ANNA, may lead to further insights into how these antibodies are possibly involved in the immunopathogenesis of IBD and autoimmune liver disease. Identification of this target antigen will also result in development of highly specific, sensitive, and repreducible assays for detection of atypical p-ANCA in routine clinical laboratory setting. These assays will have diagnostic use for patients with IBD and autoimmune liver disorders.

References

Billing, P., Tahir, S., Calfin, B., Gagne, G., Cobb, L., Targan, S., Vidrich, A. (1995). Nuclear localization of the antigen detected by ulcerative colitis associated perinuclear antineutrophil cytoplasmic antibodies. Am J Pathol, 147:979–987.

Boyum, A. (1964). Separation of white Blood Cells. Nature 204:793.

Cance, W. G., Chaudhary, N., Woman, H. J., Blobel, G., Cordon-Cando, C. ((1992). Expression of the nuclear lamins in normal and neoplastic human tissues. J Exp Clin Cancer Res 11:233–246.

Cohavy, O., Eggena, M. P., Parseghian, M., Hamkalo, B., Targan, S. R., Gordon, L. K., Braun, J., Histone H1. (1997). A candidate pANCA antigen in ulcerative colitis (abstr). Gastroenterology 112:A951.

Cohavy, O., Tayebali, A. B., Phu, P. K., Eggena, M. P., Parseghian, M. H., Hamkalo, B. A., Targan, S., Braun, J. (1998). Characterization of the pANCA cor epitope in the histone H1 C terminus (abstr). Gastroenterology 114:A953.

Collas, P., Courvalin, J. C., Poccia, D. (1996). Targeting of membranes to sea urchin sperm chromatin is mediated by a lamin B receptor-like integral membrane protein. J Cell Biol 135:1715–1725.

Collins, S. J., Gallo, R. C., Gallagher R. E. (1977). Continuous growth and differentiation of human myeloid leukemic cells in suspension culture. Nature 270:247–249.

Courvalin, J. C., Lassoued, K., Bartnik, E., Blobel, G., Wozniak, R. W. (1990). The 210-kD nuclear envelope polypeptide recognized by human autoantibodies in primary biliary cirrhosis is the major glycoprotein of the nuclear pore. J Clin Invest 86:279–285.

Courvalin, J. C., Lassoued, K., Worman, H. J., Blobel, G. (1990). Identification and characterization of autoantibodies against the nuclear envelope lamin B receptor from patients with primary biliary cirrhosis. J Exp Med 172:961–967.

Courvalin, J. C., Worman, H. J., (1997). Nuclear envelope protein autoantibodies in primary biliary cirrhosis. Semin Liver Dis 17:79–90.

Dwyer, N., Blobel, G. (1976). A modified procedure for the isolation of a pore complex-lamina fraction from rat liver nuclei. J Cell Biol 95:826–837.

Eggena, M., Targan, S. R., Iwanczyk, L., Vidrich, A., Gordon, L. K., Braun, J. (1996). Phage display cloning and characterization of an immunogenetic marker (perinuclear anti-neutrophil cytoplasmic antibody) in ulcerative colitis. J Immunol 156:4005–4011.

Fricker, M., Hollinshead, M., White, N., Vaux, D. (1997). Interphase nuclei of many mammalian cell types contain deep, dynamic, tubular membrane-bound invaginations of the nuclear envelope. J Cell Biol 136:531–544.

Gallagher, R., Collins, S., Trujillo, J. McCredie, K., Aheam, M., Tsai, S., Metzgar, R., Aulakh, G., Ting, R., Ruscetti, F., Galo, R. ((1979). Characterization of the continuous, differentiating myeloid cell line (HL-60) from a patient with acute promyelocytic leukemia. Blood 54:713–733.

Gerace, L., Ottaviano, Y., Kondor-Koch, C. (1982). Identification of a major polypeptide of the nuclear pore complex. J Cell Biol 95:826–837.

Godman, G. C., Churg, J. (1954). Wegener's granulomatosis: pathology and review of the literature. Arch Pathol 58:533–553.

Greenberger, J. S., Sakakeeny, M. A., Humphries, R. K., Eaves, C. J., Eckner, R. J. (1983). Demonstration of permanent factor-dependent multipotential (erythroid/neutrophil/basophil) hematopoietic progenitor cell lines. Proc Natl Acad Sci USA 80:2931–2935

Halbwachs-Mecarelli, L., Nusbaum, P., Noel, L. H., Reumaux, D., Erlinger, S., Grunfeld, J. P., Lesavre, P. (1992). Antineutrophil cytoplasmic antibodies (ANCA) directed against cathespin G inulcerative colitis, Crohn's disease and primary sclerosing cholangitis. Clin Exp Immunol 90:79–84.

Hofman, G. S., (1998). Classification of the systemic vasculitides: antineutrophil cytoplasmic antibodies, consensus and controversy. Clin Exp Rheumatol 16:111–115.

Johnson, P. J., McFarlane, I. G. (1993). Meeting report: international autoimmune hepatitis group. Hepatology 18:998–1005.

Laemmli, U. K., (1970) Cleavage of structural proteins during the assembly of the bacteriophage T4. Nature 224:680–685.

Lassoued, K., Guilly, M-N., Danon, F., Andre, C., Dhumeaux, D., Clauvel, J. P., Brouet, J. C., Seligmann, M., Courvalin, J. C. (1988). Antinuclear autoantibodies specific for lamins: characterization and clinical significance. Ann Intern Med 108:829–833.

Lassoued, K., Brenard, R., Degos, F., Courvalin, J. C., Andre, C., Danon, F., Brouet, J. C., Zine-el-Abidine, Y., Degott, C., Zafrani, S., Dhumeaux, D., Benhamou, J. P. (1990). Antinuclear antibodies directed to a 200-kilodalton polypeptide of the nuclear envelope in primary biliary cirrhosis. A clinical and immunological study of a series of 150 patients with primary biliary cirrhosis. Gastroenterology 99:181–186.

Lin, F., Noyer, C. M., Ye, Q., Courvalin, J. C., Worman, H. J. (1994). Autoantibodies from patients with primary biliary cirrhosis recognize a region within the nucleoplasmic domain of inner nuclear membrane protein LBR. Hepatology 23:57–61.

Lock, R. J. (1994). Detection of autoantibodies to neutrophil cytoplasmic antigens. J Clin Pathol 47:4–8.

Mizoguchi, E., Mizoguchi, A., Chiba, C., Niles, J. L., Bhan, A. K. (1997). Antineutrophil cytoplasmic antibodies in T-cell receptor alpha-deficient mice with chronic colitis. Gastroenterology 113:1828–1835.

Nickowitz, R. E., Wozniak, R. R., Schaffner, F., Worman, H. J. (1994). Autoantibodies against integral membrane proteins of the nuclear envelope in patients with primary biliary cirrhosis. Gastroenterology 106:193–199.

O'Farrell, P. H. (1975). High resolution two-dimensional electrophoresis of proteins. J Biol Chem 250: 4007–4021.

Olmsted, J. B., (1981). Affinity purification of antibodies from diazotized paper blots of heterogeneous protein samples. J Biol Chem 256:11955–11957.

Orth, T., Kellner, R., Diekmann, O., Faust, J., Meyer, zum Buschenfelde, K. H., Mayet, W. J. (1998). Identification and characterization of autoantibodies against catalase and a-enolase in patients with primary sclerosing cholangitis. Clin Exp Immunol 112:507–515.

Peen, E., Almer, S., Bodemar, G., Ryden, B. O., Sjöjlin, C., Tejle, K., Skogh, K. (1993). Anti-lactoferrin antibodies and other types of ANCA in ulcerative colitis, primary sclerosing cholangitis, and Crohn's disease. Gut 34:56–62.

Ralph, P., Moore, M. A., Nilsson, K. (1976). Lysozyme synthesis by established human and murine histiocytic lymphonoma cell lines. J Exp Med 143:1528–1533.

Roozendaal, C., Zhao, M. H., Horst, G., Lockwood, C. M., Kleibeuker, J. H., Limburg, P. C., Nelis, G. F., Kallenberg, C. G. M. (1998). Catalase and a-enolase: two novel granulocyte antigens in inflammatory bowel disease (IBD). Clin Exp Immunol 112:10–16.

Rump, J. A., Scholmerich, J., Gross, V., Roth, M., Helfesrieder, R., Rautmann, A., Ludemann, J., Gross, W. L., Peter, H. H. (1990). A new type of perinuclear anti-neutrophil cytoplasmic antibody (p-ANCA) in active ulcerative colitis but not in Crohn's disease. Immunobiology 181:406–413.

Saviage, J., Gillis, D., Benson, E., Davies, D., Esnault, V., Falk, R. J., Hagen, E. C., Jayne, D., Jennette, J. C., Paspaliaris, B., Pollock, W., Pusey, C., Savage C. O. S., Silvestrini, R., van der Woude, F., Wieslander J., Wiik, A. (1999). International consensus statement on testing and reporting of antineutrophil cytoplasmic antibodies (ANCA). Am J Clin Pathol 111:507–513.

Saxon, A., Shanahan, F., Landers, C., Ganz, T., Targan, S. (1990). A distinct subset of antineutrophil cytoplasmic antibodies is associated with inflammatory bowel disease. J Allergy Clin Immunol 86:202–210.

Smith, D. E., Fisher, P. A. (1984). Identification, development regulation, and response to heat shock of two antigenically related forms of a major nuclear envelope protein in Drosophila embryos: application of an improved method for affinity purification of antibodies using polypeptides immobilized on nitrocellulose blots. J Cell Biol 99:20–28.

Sobajima, J., Ozaki, S., Osakada, F., Uesugi, H., Shirakawa, H., Yoshida, M., Nakao, K. (1997) Novel autoantigens of perinuclear anti-neutrophil cytoplasmic antibodies (p-ANCA) in ulcerative colitis: non-histone chromosomal proteins, HMG1 and HMG2. Clin Exp Immunol 107:135–140.

Sobajima, J., Ozaki, S., Uesugi, H., Osakada, F., Inoue, M., Fukuda, Y., Shirakawa, H., Yoshida, M., Rokuhara, A., Imai, H., Kiyosawa, K., Nakao, K. (1999). High mobility group (HMG) non-histone chromosomal proteins HMG1 and HMG2 are significant target antigens of perinuclear anti-neutrophil cytoplasmic antibodies in autoimmune hepatitis. Gut 44:867–873.

Terjung, B., Herzog, V., Worman, H. J., Gestmann, I., Bauer, C., Sauerbruch, T., Spengler, U. (1998). Atypical antineutrophil cytoplasmic antibodies with perinuclear fluorescence in chronic inflammatory bowel diseases and hepatobiliary disorders colocalize with nuclear lamina proteins. Hepatology 28:332–340.

Towbin, H., Staehelin, T., Gordon, J. (1979). Electrophoretic transfer of proteins from polyacrylamide gels to nitrocellulose sheets: procedure and some applications. Proc Natl Acad Sci USA 76:4350–4354.

Truelove, S. C., Witts, J. (1976). Cortisone in ulcerative colitis. Final report of a therapeutic trial. BMJ 2:1041–1048.

Walmsley, R. S., Zhao, M. H., Hamilton, M. I., Brownlee, A., Chapman, P., Pounder, R. E., Wakefield, A. J., Lockwood, C. M. (1997). Antineutrophil cytoplasm autoantibodies against bactericidal/permeability-increasing protein in inflammatory bowel disease. Gut 40:105–109.

Wesierska-Gadek, J., Penner, E., Hitchmann, E., Sauermann, G. (1988). Antibodies to nuclear lamins in autoimmune liver disease. Clin Immunol Immunopathol 49:107–115.

Wiesner, R. H. (1998). Diagnostic criteria, clinical manifestations and natural history of primary sclerosing cholangitis. In: Krawitt, E. L, Wiesner, R. H., Nisioka, M., eds. Autoimmune liver diseases. $2^{nd}$ ed. Amsterdam, Netherlands: Elsevier Science, 381–412.

Wiik, A., (1989). Delineation of a standard procedure for indirect immunofluorescence detection of ANCA. APMIS 97 (suppl 6):12–13.

Worman, H. J., Yuan, J., Blobel, G., Georgatos, S. D., (1988). A lamin B receptor in the nuclear envelope. Proc Natl Acad Sci USA 85:8531–8534.

Worman, H. J., Evans, C. D., Blobel, G. (1990). The lamin B receptor of the nuclear envelope inner membrane: apolytopic protein with eight potential transmembrane domains. J Cell Biol 111:1535–1542.

Worman, H. J., Courvalin, J. C. (1991). Autoantibodies against nuclear envelope proteins in liver diseases. Hepatology 14:1269–1279.

Woude van der F. J., Lobatoo, S., Permin H., van der Giessen M, Rasmuseen N., Wiik, A., van Es L. A., van der Herm, G. K., (1985). The TH. Autoantibodies against neutrophils and monocytes: tools for diagnosis and marker of disease activity in Wegener's granulomatosis. Lancet 1:425–429.

What is claimed is:

1. A method for determining whether a human subject is diseased with ulcerative colitis, primary sclerosing cholangitis or autoimmune hepatitis which comprises:

(a) obtaining a suitable body fluid from a human subject;
    (b) contacting the suitable body fluid from the human subject with a nuclear envelope protein of neutrophils and myeloid cells having an apparent molecular weight of about 50,000 Daltons as estimated by SDS-polyacrylamide gel electrophoresis, an isoelectric point of approximately pH 6.0, and is capable of binding with a typical p-antineutrophil cytoplasmic antibodies (a typical p-ANCA), so as to bind a typical p-ANCA in the suitable body fluid to the said protein;
    (c) immunodetecting the bound a typical p-ANCA of step (b); and
    (d) determining the titer of a typical P-ANCA present in the suitable body fluid, wherein a titer in the range of about 1:160 to about 1:2560 indicates the human subject is diseased with ulcerative colitis, a titer in the range of about 1:2560 to about 1:5120 indicates the human subject is diseased with primary sclerosing cholangitis and a titer in the range of about 1:5120 to about 1:10240 indicates the human subject is diseased with autoimmune hepatitis.

2. The method of claim 1 wherein the suitable body fluid is serum.

3. The method of claim 2 wherein the serum is diluted to 1:160 with phosphate buffered saline.

4. The method of claim 1 wherein the contacting step (b) is performed by immunoblotting.

5. The method of claim 1 wherein the atypical p-ANCA is immunodetected with fluorescein isothiocyanate-conjugated goat anti-human IgG secondary antibodies.

6. The method of claim 1 wherein the titer range of a typical p-ANCA present in the suitable body fluid is determined by indirect immunofluorescence microscopy.

* * * * *